(12) United States Patent
Jones et al.

(10) Patent No.: US 7,230,143 B2
(45) Date of Patent: Jun. 12, 2007

(54) CHROMATOGRAPHIC METHOD FOR THE ANALYSIS OF BOTH IN PROCESS AND FINISHED SEVOFLURANE

(75) Inventors: Barry Jones, Martinez, GA (US); Ashot Khrimian, Rockville, MD (US); Joel Swinson, Evans, GA (US); Paul Cross, Aiken, SC (US)

(73) Assignee: Halocarbon Products Corporation, River Edge, NJ (US)

( * ) Notice: Subject to any disclaimer, the term of this patent is extended or adjusted under 35 U.S.C. 154(b) by 164 days.

(21) Appl. No.: 11/029,197

(22) Filed: Jan. 4, 2005

(65) Prior Publication Data

US 2005/0234268 A1    Oct. 20, 2005

Related U.S. Application Data

(60) Provisional application No. 60/534,340, filed on Jan. 5, 2004.

(51) Int. Cl.
    *C07C 41/34*    (2006.01)
(52) U.S. Cl. ...................... 568/682; 568/683
(58) Field of Classification Search .......... 568/682, 568/683
    See application file for complete search history.

(56) References Cited

U.S. PATENT DOCUMENTS

| 3,689,571 A | | 9/1972 | Regan et al. ............ 260/614 F |
| 4,966,785 A | * | 10/1990 | Springston .................. 427/489 |
| 5,262,052 A | * | 11/1993 | Rossiter et al. ............. 210/635 |
| 5,391,579 A | | 2/1995 | Baker et al. ................ 514/722 |
| 5,492,111 A | | 2/1996 | Tinker et al. .......... 128/203.12 |
| 5,679,576 A | | 10/1997 | Kawai et al. ................. 436/55 |
| 5,789,450 A | | 8/1998 | Baker et al. ................ 514/722 |
| 5,969,193 A | | 10/1999 | Terrell ........................ 568/683 |
| 6,469,219 B1 | | 10/2002 | Khrimian et al. ........... 568/683 |

OTHER PUBLICATIONS

Frank L. Dorman et al; "Rational design of gas chromatographic capillary column stationary phases"; American Laboratory; Mar. 20, 1999; pp. 22-26.

* cited by examiner

*Primary Examiner*—Rosalynd Keys
(74) *Attorney, Agent, or Firm*—Norris McLaughlin & Marcus PA

(57) ABSTRACT

A method in which organic matter found in a crude sevoflurane may be separated, identified, and quantified using a CARBOWAX™ (polyethylene glycol) capillary gas chromatographic column or an alkyl polysiloxane capillary gas chromatographic column. Also provided is a process control method for the production of sevoflurane, wherein the content of a particular component in one of the following steps is determined, and in that, assuming this as a variable, the treatment condition of the step is adjusted: 1) a step of extracting, or cooling to form two layers, and/or distilling a mixture of crude sevoflurane and hydrogen fluoride (HF) in order to isolate the majority of the sevoflurane and 2) an optional step of purifying the crude sevoflurane and 3) a step of distilling crude sevoflurane. Also provided is a method for determining the impurity level of a purified sevoflurane that is acceptable for use in human/animal anesthesia.

20 Claims, No Drawings

US 7,230,143 B2

CHROMATOGRAPHIC METHOD FOR THE ANALYSIS OF BOTH IN PROCESS AND FINISHED SEVOFLURANE

BACKGROUND OF THE INVENTION

1. Field of the Invention

The present invention relates to a gas chromatographic method of analysis for impurities found in sevoflurane (fluoromethyl 2,2,2-trifluoro-1-(trifluoromethyl)ethyl ether), which is used as a pharmaceutical, as an agricultural chemical, or as an intermediate in the preparation of pharmaceuticals or agricultural chemicals and to a monitoring of impurities by a gas chromatograph in the production process of sevoflurane and a process control thereon. More specifically, the invention relates to a process for determining the adequate removal of impurities from a crude sevoflurane so that a pharmaceutically acceptable product is ultimately obtained. The impurities may be residual starting materials, byproducts of the process, or contaminants. The invention also relates to a method for the removal of 1,1,1,3,3,3-hexafluoro-2-propanol (HFIP) from sevoflurane via an extraction process.

2. Description of Related Art

There have been several synthetic approaches to sevoflurane reported in the literature. For instance, sevoflurane can be obtained in accordance with a production method described in U.S. Pat. No. 3,689,571, which discloses the reaction of HFIP and a formaldehyde equivalent in the presence of an excess of anhydrous HF (hydrogen fluoride) to produce sevoflurane. This type of process is known to generate several other fluorinated ethers that must be removed from the crude sevoflurane, along with any unreacted starting materials, in order to obtain a pharmaceutically acceptable product. These impurities may be removed through a variety of methods known to those skilled in the art, including distillation, extraction, water washing, and acid/base washing, and the like. Efficient use of these methods, without causing further decomposition or side product formation, requires the accurate, quantitative isolation and identification of the impurities. This analytical process must be able to separate clearly the impurities in a reproducible fashion. Furthermore, the analytical process must be rapid enough to allow for the adjustment of the purification operation in a timely fashion.

U.S. Pat. No. 5,679,576 discloses the method of controlling a purification process by analyzing the impurities in a crude sevoflurane with gas chromatography, using a cross-linked cyanopropylmethylphenylsilicone capillary column, wherein the purification process is continued until the content of a designated impurity reaches a specified level. The method is applicable to a variety of purification processes.

In order to be most efficient and economical, it is preferable to use the fewest possible number of chromatographic columns for the analysis of all of the impurities that may be present in the sevoflurane. This principle holds true for the analysis of the finished product, particularly if the material is to be used in a pharmaceutical application. Thus, the preferred chromatographic column must be capable of clearly separating a variety of impurities including both low-boiling and high-boiling compounds, over a wide range of concentrations.

U.S. Pat. Nos. 5,391,579, 5,492,111 and 5,789,450, all describe gas chromatography of a sevoflurane product on a CARBOWAX™ (polyethylene glycol) column, but none of these patents make use of the column to analyze multiple impurities in the sevoflurane product. U.S. Pat. No. 5,969,193 also describes gas chromatography of a sevoflurane product on a CARBOWAX™ (polyethylene glycol) column, but the column is not a capillary column, and does not permit the resolution of very small amounts of various impurities in the sevoflurane product.

SUMMARY OF THE INVENTION

The present invention relates to a process for preparing fluoromethyl 2,2,2-trifluoro-1-(trifluoromethyl)ethyl ether (sevoflurane), wherein the process comprises:

a) reacting a reacting mixture comprising 1,1,1,3,3,3-hexafluoro-2-propanol (HFIP), hydrogen fluoride (HF) and a formaldehyde equivalent to form a first crude sevoflurane;

b) isolating a second crude sevoflurane by extraction of the first crude sevoflurane, by cooling the first crude sevoflurane to generate two layers, one of which two layers is enriched in sevoflurane, or by distilling the first crude sevoflurane;

c) optionally isolating a third crude sevoflurane by purifying the second crude sevoflurane; and d) isolating a finished sevoflurane by distilling the second crude sevoflurane or the third crude sevoflurane;

wherein at least one of steps a)–d) further comprises monitoring by gas chromatography using a capillary column, whereby at least one impurity of the process is isolated and quantitatively analyzed, and the capillary column is packed with a material selected from the group consisting of a polyethylene glycol and an alkyl polysiloxane.

In a related embodiment, the present invention also relates to a method for ascertaining the purity of a finished sevoflurane, wherein the method comprises subjecting a finished sevoflurane to gas chromatography using a capillary column, and thereby isolating and quantitatively analyzing more than one impurity of the finished sevoflurane, wherein, again, the capillary column is packed with a material selected from the group consisting of a polyethylene glycol and an alkyl polysiloxane.

DETAILED DESCRIPTION OF THE INVENTION

In step a), the formaldehyde equivalent is preferably formaldehyde, trioxane, paraformaldehyde or any other suitable material known to persons skilled in the art. Prior to carrying out step b), the first crude sevoflurane is isolated from the reacting mixture by fractionally distilling off from the reacting mixture an azeotrope of the first crude sevoflurane with HF. Such azeotrope is preferably substantially free of HFIP, which, in the context of the present invention, means only very small amounts of HFIP are present, preferably less than 1–2% by weight of HFIP, and particularly less than 1% by weight of HFIP. Such a process is described, for example, in commonly assigned U.S. Pat. No. 6,469,219, the entire contents of which are hereby incorporated by reference. The distillation process is considered to be complete when gas chromatographic analysis of the distillate shows too little sevoflurane, or too much side product/starting material, in the overhead fraction. The analytical improvement described herein, including the monitoring of the in process steps and finished sevoflurane by gas chromatography using a capillary column, whereby at least one impurity of the process is isolated and quantitatively analyzed, and the capillary column is packed with a material selected from the group consisting of a polyethylene glycol and an alkyl polysiloxane, is fully applicable to the process described in U.S. Pat. No. 6,469,219, and such application forms a part of the present invention.

In case the capillary column is packed with an alkyl polysiloxane, the alkyl polysiloxane is preferably a fluoroalkyl polysiloxane, and especially a trifluoropropyl polysiloxane.

In step b) of the process, an HF stream is separated from the desired sevoflurane by one of several methods. In one preferred embodiment of the process, the separation can be performed by mixing the initially collected azeotrope with an HF-immiscible solvent and isolating the resultant organic and inorganic phases.

In step c) of the process, which is optional, impurities, such as residual HF and HFIP, can be removed from the crude sevoflurane by any acceptable means. In a preferred embodiment, the residual HF and HFIP can be removed by a series of extraction steps. In the first step, undesired HFIP is removed by mixing the crude sevoflurane/HF-immiscible solvent solution with fresh HF and separating the resultant layers. This process is repeated until with additional fresh HF until the HFIP concentration in the organic layer is determined by gas chromatography to be less than 5 ppm. Once the HFIP concentration has been reduced to the desired level, the excess HF may be removed by washing the organic layer with water until the concentration of HF is less than 10 ppm.

In step d) of the process, the crude sevoflurane is distilled in order to remove both low-boiling and high-boiling fluorinated ethers such as bis (fluoromethyl) ether (BFME) and methyleneglycol bishexafluoroisopropyl ether (MGBE). A forecut fraction that contains the majority of the low-boiling impurities is collected and sampled periodically for analysis. When gas chromatography indicates that the overhead fraction contains less than 10 ppm of BFME, collection of the forecut is halted and collection of the purified sevoflurane is begun. The overhead stream, again, is sampled periodically for analysis. When the gas chromatograph shows more than 5 ppm of MGBE is present in the overhead material, the distillation is halted.

It will be apparent to those skilled in the art that this analytical methodology may be applied to the overall production process whether it is operated in continuous mode or it is run in a batch wise manner. On the basis of the analysis, subsequent adjustments can be made to at least one of steps a)–d) to improve the purity of the finished sevoflurane. By "finished sevoflurane" is meant a final product sevoflurane, and preferably sevoflurane of sufficient purity and quality as to be safely administrable to humans and/or animals. In a preferred embodiment, at least one of an adjustment to the step a), b), c) and an adjustment to the step d) is conducted in said method, said adjustment to step a) being conducted by subjecting said first crude sevoflurane to a first gas chromatography using a CARBOWAX™ (polyethylene glycol) capillary column or a fluoroalkyl polysiloxane column, to determine the content of HFIP and polyethers, and then adjusting the step a) depending on said content to prevent the further production of this type of impurities. Said adjustment to step b) may conducted by subjecting said second crude sevoflurane to a second gas chromatography using a CARBOWAX™ (polyethylene glycol) capillary column or a fluoroalkyl polysiloxane column, to determine the content of HFIP, and then adjusting the step c) depending on said content to decrease said content until the desired concentration of HFIP is obtained. Said adjustment to the step d) is conducted by subjecting said third crude sevoflurane to another gas chromatographic analysis using a CARBOWAX™ (polyethylene glycol) capillary column or a fluoroalkyl polysiloxane column to determine the content of various fluorinated ether byproducts, and then adjusting the step d), depending on said third content, to decrease said third content.

In another preferred embodiment of the invention, the CARBOWAX™ (polyethylene glycol) capillary column or the fluoroalkyl polysiloxane column is used to analyze finished product in order to determine the purity of the sevoflurane as Well as to quantify the amount of all of the possible impurities, such as starting materials, byproducts, or contaminants. In order to use a gas chromatography column for such a purpose, the peaks must be clearly separated, with a resolution of at least 1.5. Furthermore, for pharmaceutical applications, the column efficiency must be very high (several thousand theoretical plates) and the relative standard deviation must be no more than 2% for replicate injections (determined from the peak area ratio of sevoflurane to an internal standard). The most efficient method of analysis would use the fewest number of columns, preferably one, since this would avoid the time-consuming, labor-intensive task of method validation that is required by FDA regulations. Such an approach also reduces the number of expensive, difficult-to-maintain capillary columns that must be purchased and preserved in order to run the production process. Multiple columns require either the use of a dedicated, expensive gas chromatography instrument for each column, or the cumbersome, time-consuming, and difficult effort of switching columns in a single GC instrument.

The CARBOWAX™ (polyethylene glycol) capillary column is constructed of fused silica coated on the inner surface with bonded Carbowax 20M poly (ethylene glycol). It is commonly used in the separation and analysis of many polar compounds, including alcohols, aromatics, and other solvents, flavors, and fragrances. Its commercial product is Supelcowax 10 made by Supelco and the like. This type of column preferably may be used.

The RTX™-200 (trifluoropropylmethyl polysiloxane) capillary column is constructed of fused silica coated on the inner surface with bonded trifluoropropylmethyl polysiloxane. It is commonly used in the separation and analysis of phenols, nitrosamines, chlorinated pesticides, chlorinated hydrocarbons, and chlorophenoxy herbicides. Its commercial product is RTX-200 made by Restek and the like. This type of column preferably may also be used.

The invention will now be described in even greater detail with reference to the following non-limiting examples.

EXAMPLES

The gas chromatographic resolution for each column was determined under the following set of analytical conditions, with respect to fluoromethyl 1,1,3,3,3-pentafluoroisopropenyl ether (compound A), methyl hexafluoroisopropyl ether (MHFE), bis (fluoromethyl) ether (BFME), HFIP, sevoflurane, and MGBE. The results are shown in Tables 1 and 1a.

Analytical Conditions:
Gas Chromatograph: HP 6890
Column: Supelcowax 10 60 m×0.53 mm (ID)×1 μm
Column Temperature Profile: 35° C. for 10 min., then increase the temperature 10° C./min. to a final temperature of 200° C. and hold for 20 min.
Injection Port Temperature: 150° C.
Carrier Gas: He
Sample Size: 2 μl
Split Ratio: 2:1
Detector: FID (200° C.)
Integrator: Total Chrom Client/Server

TABLE 1

Results of GC analysis of Some Impurities Found in Sevoflurane Using a Carbowax column

| COMPOUND | RESOLUTION* |
|---|---|
| Compound A | 1.9 |
| MHFE | 1.9 |
| HFIP | 18.3 |
| MGBE | 3.0 |
| BFME | 1.0 |

*The resolution for each compound was determined by the following calculation:

$R=2(T2-T1)/W1+W2$ where T is the retention time of a particular peak and W is the peak width of the specified peak. The retention time and peak width for each compound is compared to the corresponding values for the nearest compound of interest.

The foregoing resolution should also be obtainable under the following analytical conditions with an RTX™-200 capillary column:
Gas Chromatograph: HP6890
Column: RTX-200 (trifluoropropyl methyl polysiloxane) 60M×0.53 mm ID×3 df
Temperature program: 35° C.—20 min.–10° C./min.–200° C.—30 min.
Flow: 2 ml/min.; helium as carrier gas
Injector: Split; split ratio 5:1; 110° C.
Detector: FID; 110° C.
Range: 1000 (HP-6890 GC)
Integrator: Total Chrom Client/Server
Injection Size: 4 mcl by autosampler TABLE 1a Results of GC analysis of Some Impurities Found in Sevoflurane Using a RTX™-200 (trifluoropropylmethyl polysiloxane) capillary column

| COMPOUND | RESOLUTION* |
|---|---|
| Compound A | 1.2 |
| MHFE | 1.2 |
| HFIP | 1.6 |
| MGBE | 13.0 |
| BFME | 7.2 |

Calculation

The column efficiency was found to be >11000 theoretical plates, and the relative standard deviation was found to be 1.4% for the Carbowax column (polyethylene glycol). In the case of the RTX™-200 (trifluoropropylmethyl polysiloxane) capillary column, the column efficiency was found to be 10,000 theoretical plates, and the relative standard deviation of the ratio of the sevoflurane peak to the internal standard was found to be 0.7%. These values clearly indicate that both the CARBOWAX™ (polyethylene glycol) capillary column and the RTX™-200 (trifluoropropylmethyl polysiloxane) capillary column are very capable of quantitatively separating and identifying a number of potential impurities, including both low-boiling and high-boiling compounds from sevoflurane.

Example 1

The partitions of sevoflurane and of HFIP in solvent/HF system were measured by mixing a small amount of either sevoflurane or HFIP with a two-layer mixture of equal volumes of a particular solvent and HF at 25 C. After enough mixing to reach equilibrium, the fraction of original compound found in the solvent was determined by gas chromatography and quantified using standards. The data are given in Table 2.

TABLE 2

Partition Coefficients of Sevoflurane and HFIP in solvent/HF system

| Compound | HC-0.8 oil* | 1,2,3-trichloropropane | Isooctane | Krytox** | Perfluoro-methyldecalin |
|---|---|---|---|---|---|
| Sevoflurane | 1.00 | 0.45 | 0.30 | 0.32 | 0.22 |
| HFIP | 0.01 | <0.005 | <0.005 | <0.005 | <0.005 |

*Mixture of tetrachlorobutanes, commercially available from Halocarbon Products Corporation
**1:1 Mixture of DuPont Krytox GLP 100 and K6

As Table 2 demonstrates, a large variety of solvents are capable of extracting sevoflurane from HF without extracting any significant amounts of HFIP.

It should be understood that the preceding is merely a detailed description of only a few embodiments of this invention and that numerous changes to the disclosed embodiments can be made in accordance with the disclosure herein without departing from the spirit or scope of the invention. The preceding description, therefore, is not meant to limit the scope of the invention. Rather, the scope of the invention is to be determined only by the appended claims and their equivalents.

What is claimed is:

1. A process for preparing fluoromethyl 2,2,2-trifluoro-1-(trifluoromethyl)ethyl ether(sevoflurane), said process comprising:
   a) reacting a reacting mixture comprising 1,1,1,3,3,3-hexafluoro-2-propanol (HFIP), hydrogen fluoride (HF) and a formaldehyde equivalent to form a first crude sevoflurane;
   b) isolating a second crude sevoflurane by extraction of the first crude sevoflurane, by cooling said first crude sevoflurane to generate two layers, one of which two layers is enriched in sevoflurane, or by distilling said first crude sevoflurane;
   c) optionally isolating a third crude sevoflurane by purifying said second crude sevoflurane; and
   d) isolating a finished sevoflurane by distilling the second crude sevoflurane or the third crude sevoflurane;
wherein at least one of steps a)–d) further comprises monitoring by gas chromatography using a capillary column, whereby at least one impurity of the process is isolated and quantitatively analyzed, and the capillary column is packed with at least one material selected from the group consisting of a polyethylene glycol and an alkyl polysiloxane.

2. The process according to claim 1, wherein said formaldehyde equivalent is selected from the group consisting of formaldehyde, trioxane or paraformaldehyde.

3. The process according to claim 1, wherein prior to step b), said first crude sevoflurane is isolated from said reacting mixture by fractionally distilling off from said reacting mixture an azeotrope of said first crude sevoflurane and HF.

4. The process according to claim 3, wherein said azeotrope is substantially free of HFIP.

5. The process according to claim 1, wherein said second crude sevoflurane is purified by extraction of a mixture of said crude sevoflurane and an HF-immiscible solvent with fresh HF.

6. The process according to claim 1, wherein at least one of the two steps b) or c) and step d) further comprises monitoring by gas chromatography using a capillary column, whereby in each step at least one impurity of the process is isolated and quantitatively analyzed, and the capillary column is packed with at least one material selected from the group consisting of a polyethylene glycol and an alkyl polysiloxane.

7. The process according to claim 5, which, as a result of said monitoring, further comprises subsequently adjusting at least one of steps b)–d) to improve the purity of the finished sevoflurane.

8. The process according to claim 1, wherein the capillary column is packed with a polyethylene glycol.

9. The process according to claim 1, wherein the capillary column is packed with an alkyl polysiloxane.

10. The process according to claim 9, wherein the alkyl polysiloxane is a fluoroalkyl polysiloxane.

11. The process according to claim 10, wherein the fluoroalkyl polysiloxane is a trifluoropropyl polysiloxane.

12. The process according to claim 11, wherein the trifluoropropyl polysiloxane is trifluoropropylmethyl polysiloxane.

13. A method for ascertaining the purity of a finished sevoflurane, said method comprising subjecting a finished sevoflurane to gas chromatography using a capillary column, and thereby isolating and quantitatively analyzing multiple impurities of said finished sevoflurane, wherein the capillary column is packed with a material selected from the group consisting of a polyethylene glycol and an alkyl polysiloxane.

14. The method according to claim 13, wherein the capillary column is packed with a polyethylene glycol.

15. The method according to claim 14, wherein the capillary column is packed with an alkyl polysiloxane.

16. The method according to claim 15, wherein the alkyl polysiloxane is trifluoropropylmethyl polysiloxane.

17. A method for ascertaining the purity of a crude sevoflurane, said method comprising subjecting a crude sevoflurane to gas chromatography using a capillary column, and thereby isolating and quantitatively analyzing at least one impurity of said crude sevoflurane, wherein the capillary column is packed with a material selected from the group consisting of a polyethylene glycol and an alkyl polysiloxane.

18. The method according to claim 17, wherein the capillary column is packed with a polyethylene glycol.

19. The method according to claim 17, wherein the capillary column is packed with an alkyl polysiloxane.

20. The method according to claim 19, wherein the alkyl polysiloxane is trifluoropropylmethyl polysiloxane.

* * * * *